United States Patent
Jugl et al.

(10) Patent No.: US 9,731,075 B2
(45) Date of Patent: Aug. 15, 2017

(54) CARTRIDGE HOLDER LATCH MATING TO AXIAL THROUGH OPENING OF BEARING WITH CENTRAL THREADED OPENING

(75) Inventors: Michael Jugl, Frankfurt am Main (DE); Torsten Kraft, Frankfurt am Main (DE); Daniel Vogt, Frankfurt am Main (DE); Axel Forstreuter, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/126,104

(22) PCT Filed: Jun. 14, 2012

(86) PCT No.: PCT/EP2012/061249
§ 371 (c)(1),
(2), (4) Date: Dec. 13, 2013

(87) PCT Pub. No.: WO2012/171981
PCT Pub. Date: Dec. 20, 2012

(65) Prior Publication Data
US 2014/0121606 A1  May 1, 2014

(30) Foreign Application Priority Data
Jun. 17, 2011 (EP) .................. 11170308

(51) Int. Cl.
*A61M 5/315* (2006.01)
*A61M 5/24* (2006.01)
(52) U.S. Cl.
CPC .......... *A61M 5/24* (2013.01); *A61M 5/31543* (2013.01); *A61M 5/31585* (2013.01);
(Continued)

(58) Field of Classification Search
CPC ........ A61M 2005/2407; A61M 5/3129; A61M 5/3135; A61M 2005/3132;
(Continued)

(56) References Cited

U.S. PATENT DOCUMENTS 3,790,048 A * 2/1974 Luciano ............ A61M 5/31553
222/390
4,266,541 A * 5/1981 Landau .................. A61M 5/30
604/68
(Continued)

FOREIGN PATENT DOCUMENTS

DK  WO 2011060785 A1 *  5/2011 ........ A61M 5/31551
EP  1683537  7/2006
(Continued)

OTHER PUBLICATIONS

Slot Defintion, Merriam-Webster Incorporated, 2015.*
(Continued)

*Primary Examiner* — Bhisma Mehta
*Assistant Examiner* — Matthew A Engel
(74) *Attorney, Agent, or Firm* — McDonnell Boehnen Hulbert & Berghoff LLP

(57) ABSTRACT

A drug delivery device for administering a predefined dose of a medicament comprising a housing is presented where the housing includes a body to accommodate a drive mechanism, a cartridge holder to accommodate a cartridge having a piston slidably disposed therein in an axial direction (z), and an interconnection between cartridge holder and body. The interconnection has, at least one displaceable or resiliently deformable latch element to mate with a corresponding bearing, and the latch element is displaceable or deformable in a direction (z, w) extending substantially parallel to a circumferential side wall of the body or cartridge holder.

10 Claims, 3 Drawing Sheets

(52) U.S. Cl.
CPC .............. *A61M 2005/2407* (2013.01); *A61M 2005/2492* (2013.01)

(58) Field of Classification Search
CPC .. A61M 2005/2492; A61M 2005/3131; A61M 2005/2414; A61M 2005/2411; A61M 2005/2418; A61M 5/24; A61M 5/31543; A61M 5/31585
See application file for complete search history.

(56) References Cited

U.S. PATENT DOCUMENTS

| | | | | |
|---|---|---|---|---|
| 4,425,120 A * | 1/1984 | Sampson | A61M 5/3271 | 604/198 |
| 4,581,022 A * | 4/1986 | Leonard | A61M 5/31581 | 222/391 |
| 4,710,178 A * | 12/1987 | Henri | A61M 5/31581 | 401/181 |
| 4,731,059 A * | 3/1988 | Wanderer | A61B 5/155 | 600/577 |
| 4,865,591 A * | 9/1989 | Sams | A61M 5/31553 | 222/287 |
| 4,900,311 A * | 2/1990 | Stern | A61M 5/3271 | 604/198 |
| 4,917,673 A * | 4/1990 | Coplin | A61M 5/3271 | 604/198 |
| 4,923,446 A * | 5/1990 | Page | A61M 5/3243 | 604/198 |
| 4,966,592 A * | 10/1990 | Burns | A61M 5/3271 | 604/198 |
| 4,973,318 A * | 11/1990 | Holm | A61M 5/24 | 604/208 |
| 5,112,317 A * | 5/1992 | Michel | A61M 5/24 | 222/386 |
| 5,137,511 A * | 8/1992 | Reynolds | A61M 5/284 | 604/191 |
| 5,279,585 A * | 1/1994 | Balkwill | A61M 5/3158 | 222/309 |
| 5,346,480 A * | 9/1994 | Hess | A61M 5/3271 | 604/197 |
| 5,545,147 A * | 8/1996 | Harris | A61M 5/31551 | 604/208 |
| 5,569,190 A * | 10/1996 | D'Antonio | A61D 7/00 | 604/135 |
| 5,573,513 A * | 11/1996 | Wozencroft | A61M 5/3257 | 128/919 |
| 5,591,138 A * | 1/1997 | Vaillancourt | A61M 5/3271 | 604/192 |
| 5,595,566 A * | 1/1997 | Vallelunga | A61M 5/3243 | 604/110 |
| 5,643,214 A * | 7/1997 | Marshall | A61M 5/2033 | 604/131 |
| 5,674,204 A * | 10/1997 | Chanoch | A61M 5/31535 | 604/207 |
| 5,688,241 A * | 11/1997 | Asbaghi | A61M 5/326 | 604/110 |
| 5,713,857 A * | 2/1998 | Grimard | A61M 5/31596 | 604/218 |
| 5,851,197 A * | 12/1998 | Marano | A61M 5/158 | 604/131 |
| 5,921,966 A * | 7/1999 | Bendek | A61M 5/24 | 604/207 |
| 5,938,642 A * | 8/1999 | Burroughs | A61M 5/31551 | 604/208 |
| 6,068,614 A * | 5/2000 | Kimber | A61M 5/178 | 264/478 |
| 6,599,272 B1 * | 7/2003 | Hjertman | A61M 5/315 | 604/197 |
| 6,634,076 B2 * | 10/2003 | Hjertman | F16L 25/0018 | 138/120 |
| 6,884,237 B2 * | 4/2005 | Asbaghi | A61M 5/3272 | 604/192 |
| 7,094,221 B2 * | 8/2006 | Veasey | A61M 5/31551 | 604/187 |
| 7,169,132 B2 * | 1/2007 | Bendek | A61M 5/31541 | 604/187 |
| 7,195,616 B2 * | 3/2007 | Diller | A61M 5/31566 | 604/207 |
| 7,241,278 B2 * | 7/2007 | Moller | A61M 5/24 | 604/211 |
| 7,427,275 B2 * | 9/2008 | DeRuntz | A61M 5/31551 | 604/187 |
| 7,481,977 B2 * | 1/2009 | Percival | B01L 3/5025 | 210/324 |
| 7,771,398 B2 * | 8/2010 | Knight | A61M 5/24 | 604/207 |
| 7,850,662 B2 * | 12/2010 | Veasey | A61M 5/24 | 604/207 |
| 7,918,833 B2 * | 4/2011 | Veasey | A61M 5/24 | 604/209 |
| 7,935,088 B2 * | 5/2011 | Veasey | A61M 5/24 | 604/207 |
| 7,985,201 B2 * | 7/2011 | Langley | A61M 5/20 | 604/131 |
| 7,993,301 B2 * | 8/2011 | Boyd | A61M 5/31555 | 604/211 |
| 8,128,594 B1 * | 3/2012 | Chang | A61M 5/3272 | 604/110 |
| 8,257,319 B2 * | 9/2012 | Plumptre | A61M 5/31525 | 604/211 |
| 8,945,063 B2 * | 2/2015 | Wotton | A61K 9/0019 | 604/181 |
| 9,108,031 B2 * | 8/2015 | Brandenburger | A61J 1/2096 | |
| 9,220,660 B2 * | 12/2015 | Sund | A61M 5/30 | |
| 9,242,047 B2 * | 1/2016 | Brereton | A61M 5/3158 | |
| 9,358,341 B2 * | 6/2016 | Plumptre | A61M 5/24 | |
| 9,446,195 B2 * | 9/2016 | Kramer | A61M 5/2033 | |
| 2001/0031949 A1 * | 10/2001 | Asbaghi | A61M 5/326 | 604/198 |
| 2002/0004652 A1 * | 1/2002 | Asbaghi | A61M 5/326 | 604/242 |
| 2002/0133122 A1 * | 9/2002 | Giambattista | A61M 5/3202 | 604/198 |
| 2003/0050609 A1 * | 3/2003 | Sams | A61M 5/20 | 604/208 |
| 2003/0105430 A1 * | 6/2003 | Lavi | A61M 5/2033 | 604/136 |
| 2003/0144630 A1 * | 7/2003 | Chang | A61M 5/3272 | 604/198 |
| 2004/0111064 A1 * | 6/2004 | Asbaghi | A61M 5/3272 | 604/198 |
| 2004/0127858 A1 * | 7/2004 | Bendek | A61M 5/31541 | 604/208 |
| 2004/0153003 A1 * | 8/2004 | Cicenas | A61B 10/0275 | 600/564 |
| 2004/0210199 A1 * | 10/2004 | Atterbury | A61M 5/31566 | 604/224 |
| 2004/0249348 A1 * | 12/2004 | Wimpenny | A61M 5/3158 | 604/207 |
| 2004/0260247 A1 * | 12/2004 | Veasey | A61M 5/31551 | 604/207 |
| 2005/0033244 A1 * | 2/2005 | Veasey | A61M 5/24 | 604/211 |
| 2006/0069354 A1 * | 3/2006 | Buenger | A61M 5/2033 | 604/198 |
| 2006/0189933 A1 * | 8/2006 | Alheidt | A61M 5/326 | 604/110 |
| 2006/0206057 A1 * | 9/2006 | DeRuntz | A61M 5/31551 | 604/224 |
| 2006/0264839 A1 * | 11/2006 | Veasey | A61M 5/24 | 604/209 |
| 2007/0123829 A1 * | 5/2007 | Atterbury | A61M 5/31566 | 604/207 |
| 2008/0027397 A1 * | 1/2008 | DeRuntz | A61M 5/31551 | 604/220 |
| 2008/0262436 A1 * | 10/2008 | Olson | A61M 5/2033 | 604/198 |

(56) References Cited

U.S. PATENT DOCUMENTS

| | | | |
|---|---|---|---|
| 2009/0005742 A1* | 1/2009 | Liversidge | A61M 5/326 604/263 |
| 2009/0024093 A1* | 1/2009 | Carrel | A61M 5/326 604/198 |
| 2009/0198193 A1* | 8/2009 | Veasey | A61M 5/24 604/207 |
| 2009/0264828 A1* | 10/2009 | Dette | A61M 5/31533 604/189 |
| 2010/0094205 A1* | 4/2010 | Boyd | A61M 5/31595 604/68 |
| 2010/0094206 A1* | 4/2010 | Boyd | A61M 5/31555 604/68 |
| 2010/0094207 A1* | 4/2010 | Boyd | A61M 5/31555 604/68 |
| 2010/0094253 A1* | 4/2010 | Boyd | A61M 5/31555 604/506 |
| 2010/0106098 A1* | 4/2010 | Atterbury | A61M 5/31566 604/207 |
| 2010/0114038 A1* | 5/2010 | Sams | A61M 5/2033 604/211 |
| 2010/0137792 A1* | 6/2010 | Boyd | A61M 5/31555 604/68 |
| 2010/0268170 A1* | 10/2010 | Carrel | A61M 5/2033 604/198 |
| 2010/0286623 A1* | 11/2010 | Liversidge | A61M 5/326 604/198 |
| 2010/0324494 A1* | 12/2010 | Plumptre | A61M 5/31551 604/207 |
| 2010/0324496 A1* | 12/2010 | Plumptre | A61M 5/24 604/207 |
| 2010/0324497 A1* | 12/2010 | Plumptre | A61M 5/24 604/207 |
| 2010/0324527 A1* | 12/2010 | Plumptre | A61M 5/31536 604/500 |
| 2010/0331788 A1* | 12/2010 | Plumptre | A61M 5/31543 604/207 |
| 2010/0331790 A1* | 12/2010 | Plumptre | A61M 5/31511 604/207 |
| 2010/0331791 A1* | 12/2010 | Plumptre | A61M 5/31551 604/207 |
| 2010/0331792 A1* | 12/2010 | Plumptre | A61M 5/31525 604/207 |
| 2010/0331806 A1* | 12/2010 | Plumptre | A61M 5/31543 604/500 |
| 2011/0034902 A1* | 2/2011 | Markussen | A61M 5/3156 604/506 |
| 2011/0118667 A1* | 5/2011 | Zaiken | A61M 5/3202 604/138 |
| 2011/0152784 A1* | 6/2011 | Veasey | A61M 5/24 604/207 |
| 2011/0319832 A1* | 12/2011 | Chun | A61M 5/326 604/198 |
| 2011/0319833 A1* | 12/2011 | Chun | A61M 5/326 604/198 |
| 2012/0010575 A1* | 1/2012 | Jones | A61M 5/31555 604/211 |
| 2012/0010576 A1* | 1/2012 | Raab | A61M 5/31585 604/211 |
| 2012/0022462 A1* | 1/2012 | Plumptre | A61M 5/3129 604/197 |
| 2012/0041368 A1* | 2/2012 | Karlsson | A61M 5/3272 604/111 |
| 2012/0046643 A1* | 2/2012 | Plumptre | A61M 5/31551 604/506 |
| 2012/0089098 A1* | 4/2012 | Boyd | A61M 5/24 604/189 |
| 2012/0089100 A1* | 4/2012 | Veasey | A61M 5/24 604/209 |
| 2012/0165752 A1* | 6/2012 | Holmqvist | A61M 5/31553 604/211 |
| 2012/0172816 A1* | 7/2012 | Boyd | A61M 5/31555 604/211 |
| 2012/0283649 A1* | 11/2012 | Veasey | A61M 5/31535 604/208 |
| 2012/0283651 A1* | 11/2012 | Veasey | A61M 5/31543 604/210 |
| 2012/0283652 A1* | 11/2012 | MacDonald | A61M 5/24 604/211 |
| 2012/0283653 A1* | 11/2012 | MacDonald | A61M 5/24 604/211 |
| 2012/0283654 A1* | 11/2012 | MacDonald | A61M 5/24 604/211 |
| 2012/0283655 A1* | 11/2012 | Plumptre | A61M 5/31543 604/211 |
| 2012/0283658 A1* | 11/2012 | Plumptre | A61M 5/24 604/211 |
| 2012/0283661 A1* | 11/2012 | Jugl | A61M 5/31551 604/224 |
| 2012/0283662 A1* | 11/2012 | MacDonald | A61M 5/24 604/236 |
| 2012/0289907 A1* | 11/2012 | Veasey | A61M 5/24 604/211 |
| 2012/0289908 A1* | 11/2012 | Kouyoumjian | A61M 5/31543 604/211 |
| 2012/0296286 A1* | 11/2012 | Raab | A61M 5/31593 604/211 |
| 2012/0310168 A1* | 12/2012 | Plumptre | A61M 5/31543 604/189 |
| 2012/0310206 A1* | 12/2012 | Kouyoumjian | A61M 5/31525 604/506 |
| 2013/0018327 A1* | 1/2013 | Dasbach | A61M 5/3156 604/211 |
| 2013/0030409 A1* | 1/2013 | Macdonald | A61M 5/24 604/506 |
| 2013/0184653 A1* | 7/2013 | Moller | A61M 5/31525 604/211 |
| 2013/0204186 A1* | 8/2013 | Moore | A61M 5/2448 604/111 |
| 2013/0211338 A1* | 8/2013 | Roberts | A61M 5/326 604/198 |
| 2013/0289518 A1* | 10/2013 | Butler | A61M 5/31535 604/500 |
| 2013/0324938 A1* | 12/2013 | Brereton | A61M 5/3158 604/218 |
| 2014/0012208 A1* | 1/2014 | Plumptre | A61M 5/31543 604/211 |
| 2014/0316347 A1* | 10/2014 | Veasey | A61M 5/24 604/211 |
| 2016/0206825 A1* | 7/2016 | Plumptre | A61M 5/31535 |

FOREIGN PATENT DOCUMENTS

| | | |
|---|---|---|
| WO | 2008/003560 | 1/2008 |
| WO | 2009/137486 | 11/2009 |

OTHER PUBLICATIONS

Opening Defintion, Merriam-Webster Incorporated, 2015.*
International Search Report for Int. App. No. PCT/EP2012/061249, completed Aug. 22, 2012.

* cited by examiner

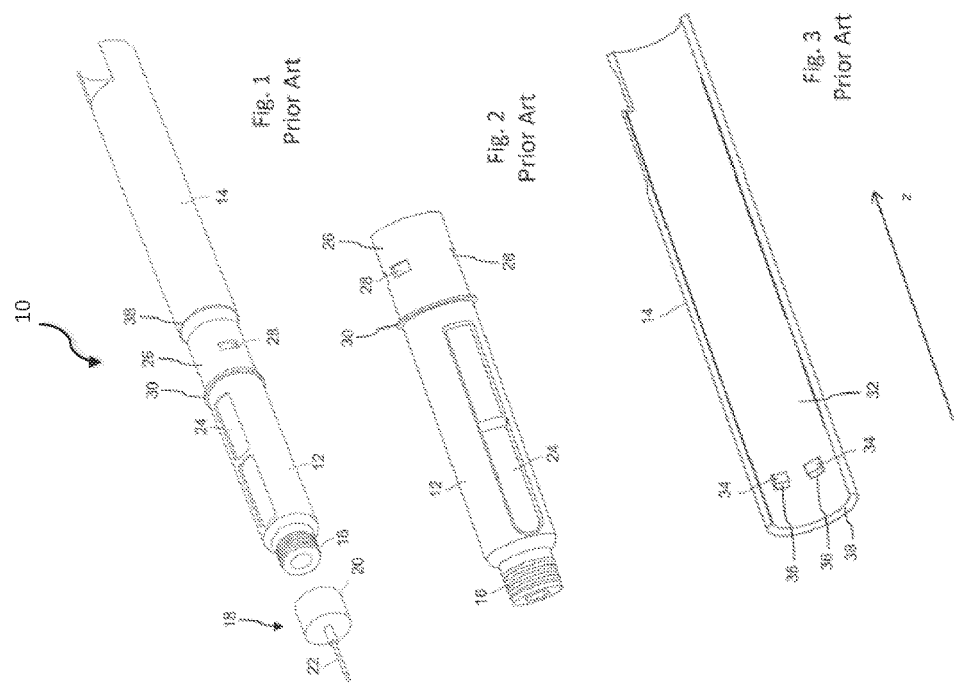

CARTRIDGE HOLDER LATCH MATING TO AXIAL THROUGH OPENING OF BEARING WITH CENTRAL THREADED OPENING

CROSS REFERENCE TO RELATED APPLICATIONS

The present application is a U.S. National Phase Application pursuant to 35 U.S.C. §371 of International Application No. PCT/EP2012/061249 filed Jun. 14, 2012, which claims priority to European Patent Application No. 11170308.8 filed Jun. 17, 2011. The entire disclosure contents of these applications are herewith incorporated by reference into the present application.

TECHNICAL FIELD

The present invention relates to the field of drug delivery devices and in particular to injection devices such like pen-type injectors for administering a predefined dose of a liquid medicament.

BACKGROUND

Drug delivery devices allowing for multiple dosing of a required dosage of a liquid medicament, such as liquid drugs, and further providing administration of the medicament to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicament to be administered is provided in a cartridge that has a moveable piston or bung mechanically interacting with a piston rod of a drive mechanism of the drug delivery device. By applying thrust to the piston in a distal direction, a predefined amount of the medicinal fluid is expelled from the cartridge.

In particular for elderly or physically infirm users, the overall handling of the device in a home medication environment should be simple and highly reliable. As for instance illustrated in FIGS. 1 to 3, drug delivery devices and in particular pen-type injectors typically comprise a multi-component housing. Here, a distal end section typically serves as a cartridge holder 12. The cartridge holder 12 comprises a threaded socket 16 at its distal end to receive a needle assembly 18 having a correspondingly threaded needle hub 20 and a double tipped injection needle 22.

The cartridge holder 12 further comprises an insert portion 26 at its proximal end section, by way of which the cartridge holder 12 can be at least partially inserted into a correspondingly shaped distal receptacle of a proximal housing component 14 of the drug delivery device, typically denoted as body 14. The body 14 serves to accommodate a drive mechanism having a piston rod to become operably engaged with a piston of a cartridge to be disposed and fixed in the cartridge holder 12. By way of the inspection window 24, the fluid or filling level of the cartridge can be visually inspected.

The known device 10 as illustrated in FIGS. 1 to 3 is of disposable type. Cartridge holder 12 and body 14 are adapted to be interconnected in a non-releasable way. For this purpose, the insert portion 26 of the cartridge holder 12 comprises several circumferentially distributed through openings 28 of substantially rectangular shape. Correspondingly and as illustrated in FIG. 3, the receiving side wall portion 32 of the body 14 comprises radially inwardly protruding pegs or prongs 34 adapted to mate with the through openings 28 of the cartridge holder as soon as the cartridge holder 12 is appropriately inserted into the body 14 with its insert portion 26.

Radially inwardly protruding prongs 34 further comprise a beveled surface 36 towards their distal end in order to facilitate mutual engagement of prongs 34 and through openings 28. Furthermore, the insert portion 26 of the cartridge holder 12 is delimited in distal direction by a circumferential and radially outwardly extending rim 30, which in a final assembly configuration abuts against a distally located end face 38 of the body 14.

The housing components 12, 14 are typically manufactured as injection moulded plastic components, which, by virtue of appropriately selected thermoplastic materials feature a sufficient elasticity in order to support the snapping in and a resulting positive interconnection of cartridge holder 12 and body 14.

However, since such drug delivery devices 10 are predominately intended for home medication, the device has to fulfill highest possible standards in terms of failure safety and robustness, especially in view of mechanical impact.

If for instance the device 10 drops down from a considerably height, a mechanical load-distribution may rise above a critical level in the interconnection of cartridge holder 12 and body 14. Point stresses or point loading acting on the through opening 28 and/or on the prongs 34 may exceed a critical level and the interconnection of cartridge holder 12 and body 14 may break down, the housing components 12, 14 may release and the device 1 would be no longer of use.

It is therefore an object of the present invention to provide a drug delivery device comprising a robust, reliable and mechanically resistant interconnection of cartridge holder and body. The interconnection should be easily integrable in existing housing designs of drug delivery devices. It should also be easily implementable, both, in terms of production costs and assembly work. Moreover, the interconnection of body and cartridge holder should be intuitive and easy to establish.

SUMMARY

The present invention relates to a drug delivery device for administering a predefined dose of a medicament. The drug delivery device, typically designed as pen-type injector comprises a housing having at least two components, a proximally located body to accommodate a drive mechanism and a distally located cartridge holder to accommodate a cartridge having a piston slidably disposed therein in an axial direction. The drive mechanism to be arranged in the body typically has a displaceable piston rod, which is adapted to operably engage with the piston of the cartridge. This way, the piston rod can exert distally directed thrust to the piston for expelling a predefined amount of the medicament from the cartridge via a distally located seal, which is typically to be penetrated by an injection needle.

Cartridge holder and body are to be directly interconnected by way of an interconnection. The interconnection is preferably of positive-engaging type and has at least one displaceable or resiliently deformable latch element which is adapted to mate and to engage with a corresponding bearing. The latch element is displaceable or deformable in a direction (z, w) extending substantially parallel to a circumferential side wall of body or cartridge holder. Typically, body and cartridge holder are of substantially cylindrical or tubular shape. The at least one latch element is therefore adapted to establish a positive interlock between cartridge holder and body by way of which a snap-in- or engaging motion can exclusively take place in the plane defined by the circumferential side walls of body or cartridge holder.

Such circumferentially directed displacement or deformation of the at least one latch element is beneficial in that mutually corresponding insert portions or receptacle portions of body and cartridge holder no longer have to provide a through opening in a circumferential side wall portion that is to engage with radially inwardly or outwardly extending prongs or the like. Hence, the circumferential displacement or deformation of the at least one latch element supports a modified and more robust design of side wall portions of cartridge holder and body. Consequently, side wall sections of said housing components that form the interconnection of cartridge holder and body can be designed free of through openings and/or latch elements.

Also, respective side wall portions of cartridge holder and body can be designed as substantially closed surfaces inherently providing increased mechanical strength, reliability and failure safety in the event of considerable mechanical impact.

Preferably, the interconnection is established by a plurality of mutually corresponding and mutually mating latch elements and bearings, that are preferably integrated or integrally formed with said housing components, cartridge holder and body.

In a preferred embodiment, cartridge holder and/or body, in particular the interconnection between cartridge holder and body comprise an insert portion and a corresponding receptacle portion for establishing an at least partially interleaved interconnection of cartridge holder and body. This way, a cartridge holder portion for instance acting as insert portion can be inserted into a receptacle portion of the body. Respective insert and receptacle portions then at least partially overlap in radial direction when a final assembly configuration is attained.

Preferably, the cartridge holder comprises the insert portion at a proximal end section and the body comprises the receptacle portion at a distal end section. This way, the cartridge holder can be at least partially inserted into the body in order to establish a positive interconnection of said housing components. However, the design of the drug delivery device is not limited to such configurations. It is generally conceivable, that the cartridge holder comprises a receptacle portion adapted to receive an insert portion of the body.

According to a further embodiment, the insert portion comprises the at least one latch element extending in longitudinal direction (z) and having at least one resiliently deformable spreading piece extending in circumferential direction (w). It may be of further benefit, when the latch element longitudinally extends from a distal end of the insert portion. Preferably, a plurality of latch elements is provided at the distal end face of the insert portion in order to intercept or to distribute mechanical impact across the circumference of the insert portion.

In a further preferred aspect, the receptacle portion comprises the at least one bearing, which extends in a lateral plane (x, y) with respect to a tubular shape of cartridge holder and/or body. Preferably, the bearing extends substantially perpendicular to the longitudinal extent of body, cartridge holder and/or insert portion and respective latch elements.

The bearing is preferably integrally formed with the receptacle portion of the body and may further delimit the receptacle portion in proximal direction. Therefore, the at least one bearing, typically extending radially inwardly from an inside facing side wall section of the body and/or of its receptacle is preferably integrally formed with the body. By way of the bearing extending in the lateral plane, any longitudinally or axially directed force effect transferred via the longitudinally extending latch element can be transferred to the bearing and may further conducted and transferred to the closed shape side wall structure of the body.

In a further preferred aspect, the bearing comprises at least one axial through opening to receive the at least one latch element of the insert portion. Preferably, the latch element may resiliently deform in order to pass through the bearing's through opening. Thereafter, circumferentially extending spreading pieces of the latch element may appropriately spread, thus preventing to retract the latch element. The latch element may also comprise an arrow-like design, wherein respective beveled shaped spreading barbs substantially inhibit a release of the interconnection of latch element and bearing. In a relaxed configuration, the through opening of the bearing is therefore smaller than the circumferential extent of the latch element. The latch element, in particular its spreading pieces or barbs have to be resiliently squeezed in order to pass through the bearing's through opening or receptacle.

The through opening of the bearing can be arranged adjacent a circumferential side wall of the receptacle portion. It may also be arranged at a radial distance from the side wall portion.

According to another embodiment, the bearing adjacently extends to an inside facing side wall section of the receptacle portion and further comprises a central through opening to axially guide a piston rod of the drive mechanism. The central through opening may be threaded in order to cooperate with an outer thread of the piston rod. Alternatively, the central through opening of the bearing or web may also comprise a radially extending groove or protrusion to mate with a radially extending rotation inhibiting protrusion or groove of the piston rod.

According to another embodiment, the latch element and the corresponding bearing are integrated in at least one longitudinally extending rib and groove of mutually engaging side wall sections of insert portion and receptacle portion of cartridge holder and body, respectively. When side wall sections of insert portion and receptacle portion are provided with mutually corresponding ribs and grooves, a torsion-resistant interconnection of body and cartridge holder can be attained.

Moreover, by way of mutually corresponding tongues and grooves in or on side wall sections of body and cartridge holder, a mutual interconnection of said housing components requires a respective rotative alignment of body and cartridge holder prior to an insertion of insert portion into the receptacle portion. Additional or adjacent to the above-described latching element, also the groove and the corresponding rib can be equipped with mutually corresponding latch elements and bearings. For instance, the longitudinal groove may comprise a circumferentially extending bearing or a respective recess adapted to mate and to engage with circumferentially extending latch elements of the rib.

Preferably, the rib and/or the groove extend in radial direction with respect to mutually corresponding side wall sections of insert portion and receptacle portion. In particular, the rib or a correspondingly shaped tongue may radially outwardly protrude from a lateral side wall section of the insert portion. Accordingly or alternatively, the rib may also extend radially inwardly from an inward facing side wall section of the receptacle portion. A corresponding and cooperating groove adapted to receive said rib is provided in the corresponding inner or outer side wall section of the receptacle or the insert portion.

In a further preferred aspect, the bearing adapted to mate with the at least one latch element comprises at least one undercutting circumferentially extending in the groove. The undercutting is designed and configured to cooperate with a spreading piece or barb of the latch element extending in circumferential direction.

It is of further benefit, when according to another embodiment side wall sections of the insert portion and/or of the receptacle portion comprise a substantially closed surface structure, which is substantially free of through openings or comparative structurally weakened areas. This way, side wall sections of insert portion and receptacle portion of body and cartridge holder can be structurally strengthened, such that they become less prone to fracture in response to mechanical impact or shock.

In a further aspect, the interconnection to be established between cartridge holder and body is of non-releasable type. Hence, once an interconnection has been established, a non-destructive release of said housing component is neither intended nor possible. Upon consumption of the medicament provided in a cartridge, the drug delivery device is intended to be discarded in its entirety.

According to another preferred aspect, the drug delivery device is equipped with a pre-filled cartridge arranged in the cartridge holder. The cartridge is at least partially filled with an injectable medicament. Also, the drug delivery device is further equipped with a drive mechanism arranged in the body, ready to exert distally directed thrust to the cartridge's piston for the purpose of precisely expelling a predefined dose or amount of the medicament.

The term "medicament," as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawings, in which:

FIG. 1 schematically illustrates a drug delivery device according to the prior art in an exploded view, FIG. 2 separately illustrates a cartridge holder shown in FIG. 1, and FIG. 3 schematically depicts a cross section through the body component according to FIG. 1.

DETAILED DESCRIPTION

Figure 4:
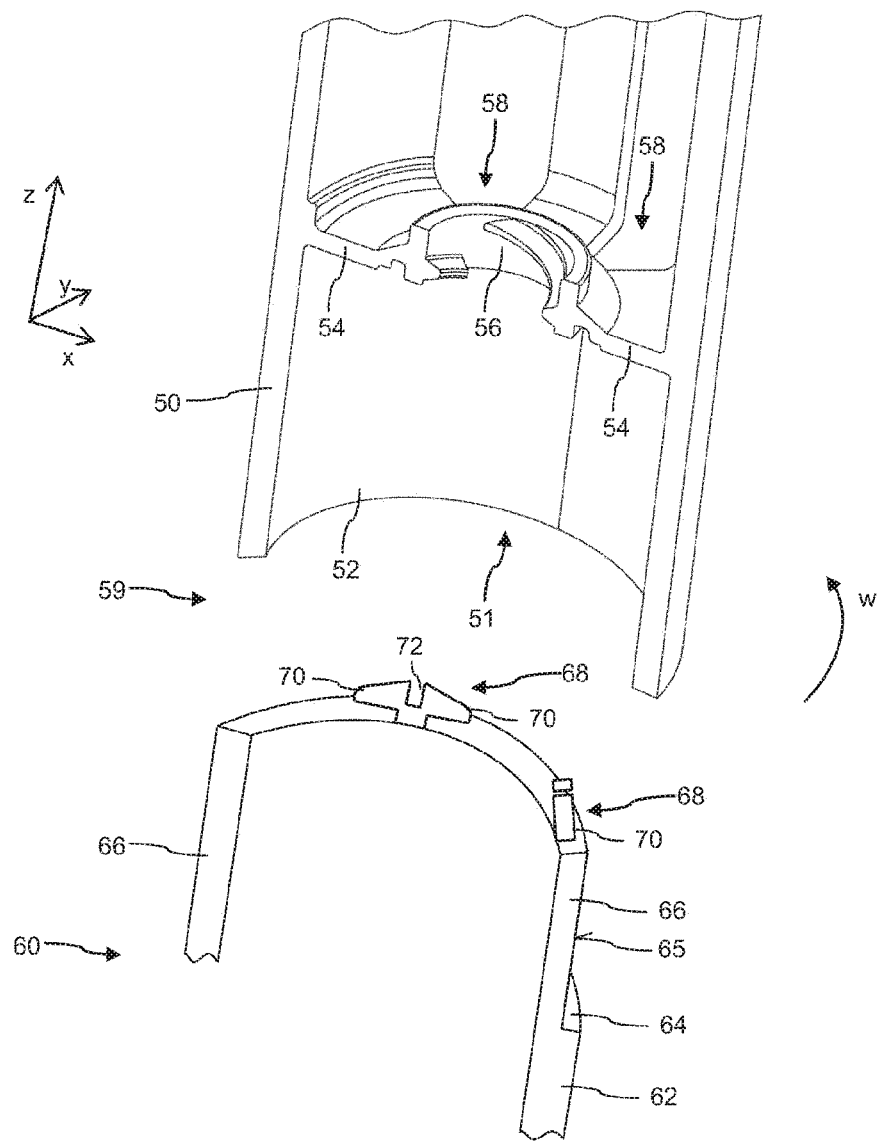
FIG. 4 is illustrative of the interconnection of body and cartridge holder according to a first embodiment of the invention, FIG. 5 schematically shows an alternative design for a latch element, FIG. 6 schematically depicts a latch element integrated in a longitudinal rib of the cartridge holder, and FIG. 7 schematically shows a positive interlock attainable by way of a latch element according to FIG. 6.

In FIG. 4, a receptacle portion 51 of a body housing component 50 is illustrated, which is adapted to receive a correspondingly shaped insert portion 66 of a cartridge holder 60. In contrast to the embodiment as illustrated in FIGS. 1 to 3, the side wall sections 52, 65 of body 50 and cartridge holder 60 substantially comprise an entirely closed surface structure, which is free of radial through openings.

The latch mechanism 59 attainable by the embodiment as illustrated in FIG. 4 is based on arrow-like latch elements 68 extending in longitudinal direction (z) from a proximalend of the insert portion 66. The body 50 comprises a tubular or cylindrically shaped side wall 52 having a bearing 54 extending in a lateral plane (x, y). The bearing 54, which also serves as a lateral web is a solid structure integrally formed with the lateral side wall 52 of the body 50 and comprises at least one axial through opening 58 which is adapted to receive and to mate with the longitudinally extending latch elements 68 of the insert portion 66.

The latch elements 68 as illustrated in FIG. 4 comprise two oppositely and circumferentially extending spreading pieces or barbs 70 that may squeeze or circumferentially deform when urged through the through openings 58 of the bearing 54. Resilient or elastic deformation of the barbs 70 can be supported by a longitudinal slit 72 extending between the circumferentially extending spreading pieces 70.

Position and circumferential distribution of the latch elements 68 corresponds with the circumferential size and position of the axial through openings 58 of the bearing 54. The bearing 54 as further illustrated in FIG. 4 also comprises a central and threaded through opening 56, that serves to axially guide a piston rod of a drive mechanism being not further illustrated here.

The latch elements 68 as shown in FIG. 4 extend in longitudinal direction (z) as well as in circumferential direction (w). They are particularly adapted to resiliently or elastically deform in circumferential direction (w) in order to establish a positive interlock with the bearing 54. This way, a mutual interconnection of body 50 and cartridge holder 60 can be attained on the basis of a positive snap-in solution without the necessity to provide through openings or other structurally weakened portions in the side wall sections 52, 65 of receptacle portion 51 and insert portion 66.

Typically, the longitudinal extension of the insert portion 66 substantially matches with the longitudinal extension of the receptacle portion 51. When a final assembly configuration of the drug delivery device is attained, cartridge holder 60 and body 50 not only abut in radial direction but also in longitudinal direction (z). It is intended, that a distal and lower end face of the body abuts 50 in longitudinal direction with a radially extending circumferential rim 64 of the cartridge holder 60. Correspondingly, also a proximally located end face of the insert portion 66 may but against the transverse or laterally extending bearing 54 in final assembly configuration. The circumferential rim 64 further separates a distal and substantially tubular shaped portion 62 of the cartridge holder 12 and the insert portion 66.

Figure 5:
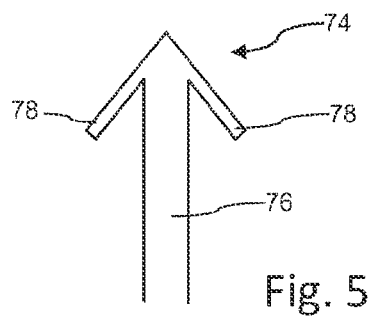

FIG. 5 shows an alternative embodiment of a latch element 74 comprising a somewhat arrow-like shape and having two beveled barbs 78 at the free end of an elongated socket portion 76. The barbs 78 are intended to mate and to abut with the proximally located surface of the bearing 54 as illustrated in FIG. 4.

Figure 6:
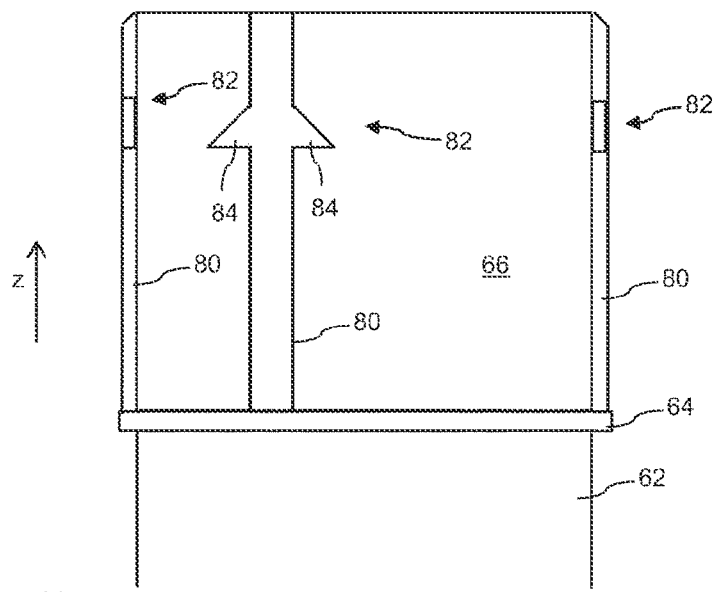
Figure 7:
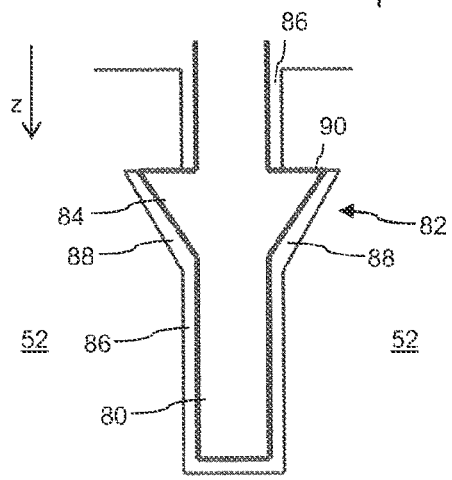

The embodiment according to FIGS. 6 and 7 is illustrative of another snap-in configuration. Here, the insert portion 66 of the cartridge holder 60 comprises substantially longitudinally extending ribs or tongues 80 with circumferentially extending latch elements 82 comprising circumferentially extending barbs 84 that mate with correspondingly shaped recesses 88 of a longitudinal groove 86 provided in the inside facing side wall section 52 of the receptacle 51 of the body component 50.

Here, it is of further benefit, when the circumferentially protruding barbs or spreading pieces 84 comprise a sufficient elasticity that allows to urge the latch elements 82 through the groove 86 in longitudinal direction (z) until a final assembly configuration as illustrated in FIG. 7 is reached. The recess 88 which is adapted to accommodate a relaxed latch element 82 comprises an undercutting 90 substantially extending in the lateral plane (z, w). However, also other embodiments are conceivable, wherein the undercutting 90 and the circumferentially protruding barbs comprise mutually corresponding abutment faces extending at an angle, substantially smaller than 90° with respect to the direction of assembly (z).

The embodiment according to FIGS. 6 and 7 can be arbitrarily combined with the embodiment according to FIG. 4 and may therefore provide an additional fixation of cartridge holder 60 and body 50 of a drug delivery device, e.g. of pen-injector type.

The invention claimed is:

1. A drug delivery device for administering a predefined dose of a medicament comprising a housing having:

a body to accommodate a drive mechanism,
a cartridge holder to accommodate a cartridge having a piston slidably disposed therein in an axial direction (z),
an interconnection between the cartridge holder and the body, said interconnection having at least one resiliently deformable latch element configured to mate with a bearing, wherein each latch element of the at least one latch element is resiliently deformable relative to the cartridge holder and relative to the body in a direction (z, w) extending substantially parallel to a circumferential side wall of the body or the cartridge holder,
wherein the cartridge holder and the body comprise an insert portion and a corresponding receptacle portion for establishing an at least partially interleaved interconnection of the cartridge holder and the body,
wherein the receptacle portion comprises the bearing, wherein the bearing comprises a solid structure extending in a lateral plane (x, y) with respect to a tubular shape of the cartridge holder or the body, wherein the solid structure extends radially inward from an inside facing side wall section of the receptacle portion and defines a lateral web, and
wherein the lateral web comprises at least one axial through opening to receive the at least one latch element and wherein a radial center of the lateral web comprises a central and threaded through opening being threaded to cooperate with an outer thread of a piston rod of the drive mechanism.

2. The drug delivery device according to claim 1, wherein the cartridge holder comprises the insert portion to be inserted into the receptacle portion of the body, or vice versa.

3. The drug delivery device according to claim 1, wherein the insert portion comprises the at least one latch element extending in longitudinal direction (z) and having at least one resiliently deformable spreading piece extending in a circumferential direction (w).

4. The drug delivery device according to claim 1, wherein the bearing adjacently extends to the inside facing side wall section of the receptacle portion.

5. The drug delivery device according to claim 1, wherein side wall sections of the insert portion and/or of the receptacle portion comprise a closed surface structure, free of through openings.

6. The drug delivery device according to claim 1, wherein the interconnection is of non-releasable type.

7. The drug delivery device according to claim 1, further comprising a cartridge filled with a medicament disposed in the cartridge holder.

8. The drug delivery device according to claim 1, wherein the lateral web extends across an inner diameter of the receptacle portion.

9. The drug delivery device according to claim 1, wherein the bearing is integrally formed with the receptacle portion and wherein the bearing delimits the receptacle portion in an axial direction.

10. The drug delivery device according to claim 1, wherein the at least one axial through opening of the lateral web adjoins the inside facing side wall section of the receptacle portion.

* * * * *